United States Patent [19]

Kettner et al.

[11] Patent Number: 4,644,055

[45] Date of Patent: Feb. 17, 1987

[54] METHOD FOR PREPARING SPECIFIC INHIBITORS OF VIRUS-SPECIFIED PROTEASES

[75] Inventors: Charles A. Kettner; Bruce D. Korant, both of Wilmington, Del.

[73] Assignee: E. I. Du Pont de Nemours and Company, Wilmington, Del.

[21] Appl. No.: 682,296

[22] Filed: Dec. 17, 1984

[51] Int. Cl.$^4$ ............................................. C07K 5/10
[52] U.S. Cl. ................... 530/330; 530/324; 530/350
[58] Field of Search ................ 260/112.5 R; 530/330, 530/324, 350

[56] References Cited

U.S. PATENT DOCUMENTS 4,511,504  4/1985  McCullagh et al. ......... 260/112.5 R
4,518,528  5/1985  Rasnick ...................... 260/112.5 R

OTHER PUBLICATIONS

Korant, "Inhibition of Viral Protein Cleavage", in *Antiviral Chemotherapy*, Gauri, ed., (Academic Press, New York, 1981).

Korant, "Regulation of Animal Virus Replication by Protein Cleavage", in *Proteases and Biological Control*, (Cold Spring Harbor Laboratory, 1975).

Korant et al., "Picornaviruses and Togaviruses: Targets for Design of Antivirals", in *Targets for the Design of Antiviral Agents*, De Clercq et al., eds., (Plenum, New York, 1984).

Korant, *J. Virol.*, 10:751–759 (1972).

Summers et al., *J. Virol.*, 10:880–884 (1972).

Korant et al., *Proc. Natl. Acad. Sci. USA*, 76:2992–2995 (1979).

Lozitskii et al., *Usp. Sovrem. Biol.*, 93:352–362 (1982).

Powers, "Haloketone Inhibitors of Proteolytic Enzymes", in *Chemistry and Biochemistry of Amino Acids, Peptides, and Proteins*, Weinstein, ed., (Marcel Dekker, New York, 1977) pp. 65–178.

Powers et al., *Biochim. Biophys. Acta*, 480:246–261 (1977).

Enzyme Systems Products: Nov. 1981 product bulletin.

Ito et al., *Biochem. Biophys. Res. Commun.*, 49:343 (1972).

Fittkau et al., "Synthesis and Properties of Peptide Ketones", in *Peptides 1982*, Blaha et al., eds., (de Gruyter, New York, 1983) pp. 617–622.

*Primary Examiner*—Delbert R. Phillips

[57] ABSTRACT

A general method for preparing specific inhibitors of virus-specified proteases is disclosed. The inhibitors comprise a halomethyl ketone or methyl ketone moiety covalently linked to a peptide sequence of three, four or five amino acids or amino acid residues, which peptide sequence corresponds to an amino acid sequence found adjacent to and upstream of a cleavage site recognized by a virus-specified protease.

9 Claims, 2 Drawing Figures

FIG. 2

Picornaviruses

Poliovirus
(nascent)
leu thr thr tyr/gly phe gly his
asp ala met tyr/gly thr asp gly Poliovirus
(intermediate)
pro arg leu gln/gly leu pro val*
ala leu ala gln/gly leu gly gln*
ala leu phe gln/gly pro leu gln*
ala met gln gln/gly ile thr asn
val ile lys gln/gly asp ser trp
ala gly his gln/gly ala tyr thr Poliovirus
(maturation)
pro met leu asn/ser pro asn ile FMDV
(structural)
pro ser lys gln/gly ile phe pro
pro arg thr gln/thr thr ser thr
lys gln leu leu/asn phe asp leu FMDV
(non-structural)
glu/gly leu ile val FMDV
(maturation)
ala leu leu ala/asp lys lys thr

Alphaviruses

| | | |
|---|---|---|
| Core/E3 (nascent) | ser glu glu trp/ser ala pro leu<br>thr • • •/ • • • • | SFV<br>Sindbis |
| 6K/E1 (nascent) | ala pro val ala/cys ile leu ile<br>lys val asp •/tyr gln his ala | SFV<br>Sindbis |
| E3/E2 | arg his arg arg/ser val ser gln<br>• ser lys •/ • • ile asp | SFV<br>Sindbis |
| E2/6K | arg ala his ala/ala ser val ala<br>ser • asn •/glu thr phe thr | SFV<br>Sindbis |

METHOD FOR PREPARING SPECIFIC INHIBITORS OF VIRUS-SPECIFIED PROTEASES

BACKGROUND OF THE INVENTION

The present invention relates generally to methods of treating viral infection, and particularly to methods for preparing specific peptide inhibitors of virus-specified proteases.

Proteases are enzymes which cleave proteins at specific peptide bonds. In living systems, highly specific proteases and complementary protease inhibitors mediate or control a broad spectrum of biological functions. For example, proteases cleave precursors to form active proteins in post-translational processing of polypeptides, provide mechanisms for zymogen activation cascade reactions such as blood coagulation, fibrinolysis, and complement reactions of the immune system, and mediate transport of selected proteins across biological membranes. Accordingly, proteases represent potential targets for therapeutic agents designed to function as specific inhibitors of protease activity.

Proteases encoded by viral genomes play a critical role in replication of many viruses. Viral proteases cleave large precursor polypeptides, produced by infected cells, into smaller protein components, or subunits, which are subsequently assembled to form functional virus structures. Lozitskii et al., *Usp. Sovrem. Biol.* 93:352–362 (1982), discuss the role of proteolysis in replication of avian and mammalian viruses, and have surveyed part of the literature relating to viral protease inhibitors.

Post-translational processing of viral polypeptides by a virus-specified protease occurs in replication of several important families of animal viruses, including the following:

| Virus Family | Representative Genera |
|---|---|
| Picornaviruses | poliovirus |
| | rhinovirus |
| | coxsackievirus |
| | foot-and-mouth disease virus |
| | hepatitis A virus |
| | cardiovirus |
| Togaviruses | rubella virus |
| | yellow fever virus |
| | dengue virus |
| | equine encephalitis virus |
| RNA tumor viruses | retroviruses |
| | oncoviruses |
| Adenoviruses | various types |

A role for a virus-specified protease has also been proposed in replication of other virus families, notably myxoviruses, paramyxoviruses, vaccinia viruses, comoviruses, and reoviruses. Korant, "Inhibition of Viral Protein Cleavage", in *Antiviral Chemotherapy*, Gauri, ed., (Academic Press, New York, 1981) and Korant, "Regulation of Animal Virus Replication by Protein Cleavage", in *Proteases and Biological Control*, (Cold Spring Harbor Laboratory, 1975) are reviews of literature relating to virus-specified proteases.

Picornaviruses, which are important pathogens in man and animals, are exemplary of viruses which encode a specific protease involved in viral reproduction. Picornaviruses are small, non-enveloped, RNA-containing viruses which are important pathogens in man and other mammals. Prototypical of the picornavirus group are polioviruses, which are the causative agents of poliomyelitis, a well-known and devastating disease of the central nervous system. In previous decades, poliovirus epidemics caused paralytic disease in thousands of children and young adults, spurring research which led to effective immunization and near-eradication of the disease in industrialized Western nations. Today, in densely-populated regions where sanitation is primitive, poliovirus remains widespread. Although some children are affected, the majority of the population in such areas have antibodies to the major poliovirus types. In Western countries, however, the virus is much less prevalent. Occasionally, clinically significant cases arise among non-immunized individuals.

Other picornaviruses affecting man include coxsackie viruses, which have been associated with mild intestinal infections; rhinoviruses, which are associated with colds and minor respiratory infections; hepatitis A virus; and cardioviruses, implicated in encephalomyocarditis.

Foot-and-mouth disease viruses (FMDV) are a genus of picornaviruses which afflict cattle and other cloven-hooved animals. Foot-and-mouth disease is extremely contagious, and entire herds containing infected animals are destroyed when an outbreak of the disease is confirmed. The economic consequences of a foot-and-mouth disease epidemic can thus be quite severe. Vaccines have been produced which confer a measure of protection against infection by FMDV, but the disease persists in many areas.

The picornaviruses follow a generally similar pattern of replication. First, infectious virus particles bind non-covalently to specific receptors on the surface of a target cell. Virus particles then penetrate the cell membrane and uncoat a single-stranded viral RNA molecule. This positive-stranded RNA initially serves as an mRNA template for synthesis of viral proteins, including a viral RNA polymerase. The viral RNA polymerase catalyzes synthesis of minus-stranded, or complementary, RNA's, which serve as templates for subsequent production of additional plus strands. As the process of infection proceeds, proportionately more of the newly-synthesized plus strands are incorporated into mature virions.

In addition to a viral RNA polymerase, the viral genome also specifies four major capsid structural proteins, designated $VP_1$, $VP_2$, $VP_3$ and $VP_4$; an RNA capping protein designated $VP_G$; and several non-structural proteins, including a virus-specified protease. The virus-specified protease plays a unique role in picornavirus replication, and provides a target for design of antiviral compounds which inhibit virus-specified protease activity.

Following a virus-induced shutdown of host cell protein synthesis, viral mRNA is translated to viral protein in a continuous passage of host ribosomes along viral mRNA templates. The resulting translation product is a polyprotein containing several domains, each having a different function. This polyprotein is cleaved, prior to dissociation of the ribosome/protein complex, by host cell and virus-specified proteases. Nascent cleavage reactions, which occur essentially instantaneously, are apparently mediated by cellular proteases associated with the host cell translation apparatus. A series of intermediate cleavage reactions, which induce conformational changes and other alterations in tertiary structure eventually culminating in capsid assembly, are then catalyzed by a highly specific, virus-coded protease. Proteolytic cleavages also regulate RNA synthesis by activating and deactivating the viral RNA polymerase.

The existence of a unique, virus-specified protease in cells infected by picornavirus has been demonstrated by several lines of inquiry. First, as detailed below, the virus-specified protease activity is highly site-specific, and does not resemble the proteolytic activity associated with normal cellular degradative pathways. Second, this site-specific enzyme activity is not detected in extracts of uninfected cells, but is found in lysates of infected cells in quantities which increase both as the process of infection proceeds, and as the quantity of infecting virus is increased. Third, cell-free protein synthesizing systems, programmed with viral mRNA, produce a characteristic protease activity which also processes capsid polypeptides. Fourth, it has been demonstrated in both infected cells and in cell-free systems that the viral protease is not efficient at cleaving proteins of heterologous viruses or cellular proteins.

As noted above, the virus-specified protease is highly site-specific. In the past several years, the amino acid sequences of cleavage sites recognized by virus-specified proteases have been determined for several picornaviruses. This data has been in part provided by end-group analyses of viral proteins, but additional information has been provided by sequencing viral genomic RNA, or DNA complementary to viral RNA. Comparisons of cleaved sites in picornaviruses have revealed several classes of cleavage recognition sites. The nascent cleavage sites processed essentially instantaneously during translation resemble chymotrypsin cleavage sites; new carboxyl termini are typically donated by aromatic or hydrophobic residues. Intermediate, or subsequently-processed cleavage sites, which are recognized by a virus-specified protease, are quite distinct. In the case of picornaviruses, these sites are characterized by a glutamine-glycine or glutamic acid-X linkage, frequently surrounded by hydrophobic (leucine, isoleucine, or valine) sequences. A high degree of conservation among the cleavage site sequences recognized by virus-specified protease suggests that artificial substrates, designed to mimic the structure of the conserved sequence, can be employed to inhibit specific protease activity, and hence, disrupt the process of picornavirus replication.

A number of workers have sought specific inhibitors of picornavirus protease activity. Korant, *J. Virol.* 10: 751-759 (1972), discloses inhibition of poliovirus and echovirus-12 protein processing by chloromethyl ketone derivatives of simple amino acids. Specifically, Korant discloses inhibition by tolylsulfonylphenylalanyl chloromethyl ketone (TPCK) and tolylsulfonyllysyl chloromethyl ketone (TLCK). Summers et al., *J. Virol.* 10: 880-884 (1972), similarly disclose inhibition of protease cleavage of large poliovirus-specific polypeptides by TPCK, TLCK, and D- and L-isomers of carbobenzyloxyphenylalanyl chloromethyl ketone (ZPCK). In a subsequent report, Korant et al., *Proc. Natl. Acad. Sci. USA* 76:2992-2995 (1979), describe inhibition of poliovirus protein processing by carbobenzyloxyleucyl chloromethyl ketone (ZLCK).

Togaviruses are a family of RNA-containing viruses, typically arthropod-borne, which include the pathogens of yellow fever, rubella (measles), dengue fever, encephalitis, and certain subclinical conditions. Like picornaviruses, togaviruses employ protein cleavages to form all viral polypeptides, and evidence exists that a specific protease is coded by the togavirus genome. As in the case of picornaviruses, highly conserved peptide regions are observed at cleavage sites of viral precursor polypeptides, suggesting a role for a virus-specified protease.

RNA-containing tumor viruses, or retroviruses, include a number of genera linked to various sarcomas, leukemias, lymphomas and other carcinomas in avian and mammalian species. Adenoviruses are DNA-containing viruses which induce latent infections in lymphoid tissues, which occasionally erupt into acute episodes of respiratory and ocular infection. Like picornaviruses and togaviruses, retroviruses and adenoviruses appear to encode a specific viral protease.

Various peptide derivatives with capacity to inhibit protease activity are known. Powers, "Haloketone Inhibitors of Proteolytic Enzymes", in *Chemistry and Biochemistry of Amino Acids, Peptides, and Proteins,* Weinstein, ed., (Marcel Dekker, New York, 1977), pp. 65-178, has surveyed the literature relating to inhibition of protease activity by haloketone derivatives of amino acids and peptides. Powers et al., *Biochim. Biophys, Acta* 480: 246-261 (1977), disclose inhibition of subtilisin BPN', a bacterial protease, by a series of peptide chloromethyl ketones. Of the compounds tested, acetyl-L-phenylalanyl-L-glycyl-L-alanyl-L-leucyl cholrmethyl ketone (Ac-Phe-Gly-Ala-LeuCH$_2$Cl) was the fastest inhibitor. A related compound, methoxysuccinyl-L-phenylalanyl-L-glycyl-L-alanyl-L-leucyl chloromethyl ketone (MeOSuc-Phe-Gly-Ala-LeuCH$_2$Cl), is disclosed by Enzyme Systems Products in a November 1981 product bulletin.

Ito et al., *Biochem. Biophys, Res. Commun.* 49: 343-349 (1972), describe experiments involving inhibition of chymotrypsin, a digestive protease, by certain peptide aldehydes. Ito et al. also tested for inhibition of chymotrypsin by Ac-Leu-Leu-PheCH$_3$, a tripeptidyl methyl ketone. However, no inhibition was observed at an inhibitor concentration of 600 μg/mL.

Finally, Fittkau et al., "Synthesis and Properties of Peptide Ketones", in *Peptides* 1982, Blaha et al., eds., (de Gruyter, New York, 1983) pp. 617-622, disclose inhibition of thermitase, a thermostable serine protease of *Thermoactinomyces vulgaris,* by certain peptide methyl ketones.

A general method for preparing inhibitors of virus-specified proteases has now been established. This method represents a new approach to treatment of viral infection in animals.

SUMMARY OF THE INVENTION

The present invention provides a process for preparing a specific inhibitor of proteases which cleave virus-specified polypeptide precursors to form virus-associated proteins, wherein the proteases to be inhibited are specified by a virus selected from the group consisting of picornaviruses, togaviruses, RNA tumor viruses, adenoviruses, comoviruses, and other viruses which encode a viral protease, comprising:

(a) isolating viral protein, RNA, DNA, mRNA, or DNA complementary to viral RNA;

(b) analyzing the protein, RNA, DNA, mRNA, or cDNA to provide an amino acid sequence of a polypeptide precursor of virus-specified proteins;

(c) locating within the amino acid sequence a cleavage recognition site for the virus-specified protease; and (d) preparing a specific peptide inhibitor of the virus-specified protease, wherein the inhibitor comprises a C-terminal inhibitor moiety selected from the group consisting of halomethyl ketones and methyl ketones, covalently linked to a peptide sequence of three to five amino acids or amino acid analogues which substantially corresponds to the amino acid sequence located immediately adjacent to and upstream of the cleavage recognition site of the polypeptide precursor.

DETAILED DESCRIPTION OF THE INVENTION

The method of the present invention provides selected tri-, tetra-, and pentapeptides having C-terminal halomethylketone or methylketone moieties. These compounds, which are capable of binding to the active site of virus-specified proteases, inhibit processing of viral polypeptides by the viral proteases.

The compounds prepared according to the method of the present invention are peptide halomethylketones and peptide methylketones of the following formula:

$$R^1-A_n^4-A_o^3-A^2-A^1-NHCHCCH_2X, \quad (I)$$
$$\underset{R^2}{|}$$

or physiologically acceptable salts thereof, wherein
- $A^1$, $A^2$, $A^3$ and $A^4$ are amino acids or amino acid analogues, the identity and sequence of which, taken together with the value of substituent $R^2$, substantially correspond to the amino acids located immediately adjacent to and upstream of a cleavage recognition site of a virus-specified protease;
- $R^1$ is —H or an N-terminal protecting group;
- $R^2$ is a side-chain group of an amino acid or amino acid analogue;
- X is —H, —Cl, or —Br; and
- n and o are independently 0 or 1.

Preferably, the sequence of the peptide inhibitor is exactly homologous to the amino acid sequence immediately adjacent to and upstream of the cleavage recognition sites of the polypeptide precursor. As used herein, "upstream" means in the direction which is the reverse of the direction of translation.

The term "substantially corresponds," as employed throughout the specification in relation to particular peptide sequences, indicates that a subject peptide sequence comprises a like number of amino acid residues as a reference sequence, the identity and sequence of which are exactly homologous or conservatively substituted in relation to the reference sequence. The term "conservatively substituted" as used herein denotes that a given residue has been replaced by a biologically similar residue. Examples of conversion substitution include substitution of one aliphatic residue for another, such as Ile, Val, Leu, or Ala for one another, or substitution of one polar residue for another, such as between Lys and Arg; Glu and Asp; or Gln and Asn. As used above, "residue" means either an amino acid or amino acid analogue.

As previously noted, the amino acid sequences of peptide inhibitors prepared by the process of the present invention are established by reference to amino acid sequences of cleavage sites recognized by virus-specific proteases. This data can be derived using two general techniques. First, viral proteins can be isolated from purified virus particles or infected cells and dissociated into constituent polypeptides, which are then sequenced from both N- and C-terminals by conventional protein sequence analysis methods (e.g., Edman degradation). This method provides sequence data immediately adjacent to known cleavage sites. Second, RNA genomes (or a cDNA transcript thereof) of certain viruses can be sequenced to provide a primary sequence of nucleotides, from which viral protein sequences are derived using the open reading frame of translation. Cleavage sites are then determined by comparison of the derived amino acid sequences with those of known proteins of homologous or related viruses.

Methods of obtaining and purifying viral proteins or nucleic acids, and of sequencing viral nucleic acids, are well-known, and will not be detailed herein. The following are useful general references relating to suitable methods and are hereby incorporated by reference.

Maxam, A. M., and Gilbert, W., *Proc. Natl. Acad. Sci USA* 74: 560–564 (1977).

Sanger, F., Nickler, S., and Carlson, A. R., *Proc. Natl. Acad. Sci. USA* 74:5463–5467 (1977).

Peattie, D. A., *Proc. Natl. Acad. Sci. USA* 76:1760–1764 (1979).

Simoncsits, A., Brownlee, G. G., Brown, R. S., Rubin, J. R., and Guilly, H., *Nature* 269:833–836 (1977).

The references set forth below describe sequencing experiments involving genomes or proteins of particular viruses:

1. Carroll, A. B., Rowlands, D. J., and Clarke, B. E., *Nucleic Acids Res.* 12:2461 (1984); (foot-and-mouth disease virus).

2. Herbert, E., and Muhler, M., *Cell* 30:1 (1982); (alphavirus).

3. Klenk, H. D., Garten, H. D. Keil, W., Niemann, H., Scwarz, R. T., and Rott, R., "Processing of the Influenza Virus Hemagglutinin," in G. Koch and D. Ricter, eds., *Biosynthesis, Modification, and Processing of Cellular and Viral Polyproteins* (Academic Press, New York, 1980).

4. Korant, B., Chow, N., Lively, M., and Powers, J., *Proc. Natl. Acad. Sci. USA* 76:2992 (1979); (poliovirus).

5. Korant, B., *J. Virol.* 10:751 (1972); (poliovirus).

6. Lee, T. H., Coligan, J. E., Homma, T., McLane, M. F. Tachibana, N., and Essex, M., *Proc. Natl. Acad. Sci. USA* 81:3856 (1984); (Human T-cell leukemia virus).

7. Oroszlan, S., Henderson, L. E., Copeland, T. D., Schultz, A. M., and Rabin, E. M., "Processing and Structure of Murine Leukemia Virus gag and env Gene Encoded Polyproteins," in G. Koch and D. Richter, eds., *Biosynthesis, Modification, and Processing of Cellular and Viral Polyproteins* (Academic Press, Inc., New York, 1980).

8. Palmenberg, A. C. Kirby, E. M., Janda, M. R., Drake, N. L. Duke, G. M., Potratz, K. F., and Collett, M. S., *Nucleic Acids Res.* 12:2969 (1984); (encephalomyocarditis virus)

9. Seiki, M. Seisuke, H., Hirayama, Y., and Yoshida, M., *Proc. Natl. Acad. Sci. USA* 80:368 (1983); (Human T-cell leukemia virus).

10. Stanway, G., et al., *Nucleic Acids Res.* 11:3629 (1983); (poliovirus).

11. Strauss, E. G., Rice, C. M., and Strauss, J. H., *Virology* 133:92 (1984); (Sindbis virus).

As used throughout the specification, the following abbreviations for amino acid residues or amino acids apply:

| Amino Acid | One-Letter Abbreviation | Three-Letter Abbreviation |
|---|---|---|
| L-alanine | A | Ala |
| L-arginine | R | Arg |
| L-asparagine | N | Asn |
| L-aspartic acid | D | Asp |
| L-cysteine | C | Cys |
| L-glutamine | Q | Gln |
| L-glutamic acid | E | Glu |
| glycine | G | Gly |
| L-histidine | H | His |
| L-isoleucine | I | Ile |
| L-leucine | L | Leu |
| L-lysine | K | Lys |
| L-methionine | M | Met |
| L-phenylalanine | F | Phe |
| L-proline | P | Pro |
| L-serine | S | Ser |
| L-threonine | T | Thr |
| L-tryptophan | W | Trp |
| L-tyrosine | Y | Tyr |
| L-valine | V | Val |

Where prefixed by "D-", the foregoing abbreviations indicate an amino acid of D-configuration.

As used throughout the specification, "N-terminal protecting group" means an arylcarbonyl, alkylcarbonyl, alkoxycarbonyl, aryloxycarbonyl, aralkoxycarbonyl, arylsulfonyl, alkylsulfonyl, or arylsulfonyl peptide protecting group, or other equivalents known to those skilled in the art of peptide synthesis. Gross and Meienhofer, eds., *The Peptides*, Vol. 3, (Academic Press, New York, 1981) pp. 3–81, the disclosure of which is hereby incorporated by reference, describe numerous suitable amine protecting groups. As used herein, either individually or as part of a larger group, "alkyl" means a linear, cyclic, or branched-chain aliphatic moiety of 1 to 10 carbon atoms; "substituted alkyl" means an alkyl group having a substituent containing a heteroatom or heteroatoms such as N, O or S; "aryl" means an aromatic moiety, e.g., phenyl, of 6 to 18 carbon atoms, unsubstituted or substituted with one or more alkyl, substituted alkyl, nitro, alkoxy, or halo groups; and "alkaryl" means an aryl moiety of 7 to 19 carbons having an aliphatic substituent, and, optionally, other substituents such as one or more alkyl, substituted alkyl, alkoxy or amino groups. "Aralkyl" means a linear or branched-chain aliphatic moiety of 6 to 18 carbon atoms comprising an aryl group or groups. As used herein, "halo" means Cl or Br.

Examples of suitable values for N-terminal protecting group $R^1$ formyl, acetyl, trifluoroacetyl, benzyloxycarbonyl (carbobenzoxy), substituted benzyloxycarbonyl, tert-butyloxycarbonyl, isopropyloxycarbonyl, allyloxycarbonyl, phthaloyl, benzoyl, acetoacetyl, chloroacetyl, phenoxycarbonyl, methoxysuccinyl, succinyl, 2,4-dinitrophenyl, dansyl, p-methoxybenzenesulfonyl, p-toluenesulfonyl, methanesulfonyl and phenylthio.

Certain values for N-terminal protecting group $R^1$ are abbreviated as follows throughout the specification:

| | |
|---|---|
| Z | Carbobenzoxy |
| Boc | t-Butyloxycarbonyl |
| Ac | Acetyl |
| Et | Ethyl |
| Suc | Succinyl |
| MeOSuc | Methoxysuccinyl |
| DNS | Dansyl |
| DNP | 2,4-Dinitrophenyl |

Compounds having side-chain amino groups can optionally comprise suitable N-terminal protecting groups attached to the side chains; similarly, amino acid residues having acidic or hydroxy side chains can be protected in the form of benzyl or other suitable esters or ethers.

As noted previously, $A^1$ through $A^4$ can be amino acids of D-configuration or analogues of amino acids. As used throughout the specification, "analogue" means a residue of the formula (II)

which is not a naturally-occurring amino acid. $R^3$ in the foregoing formula II can be an alkyl, substituted alkyl, aryl, aralkyl, or alkaryl group, optionally terminating in a hydroxy, amino, phosphate, or thio group. Examples of such analogues include hydroxyproline, t-carboxyglutamate, O-phosphorine, carnitine, cysteic acid, phenylglycine, α-aminoisobutyric acid and α-aminocaproic acid.

Physiologically acceptable salts of compounds of formula I include acid addition salts of free base, if present, wherein the acid can be organic or inorganic, e.g., hydrochloric, phosphoric, maleic, acetic, citric, succinic, etc. Alternatively, salts of free peptidic acids, including sodium, potassium, and ammonium salts, are included within the scope of the present invention.

Figure 1:
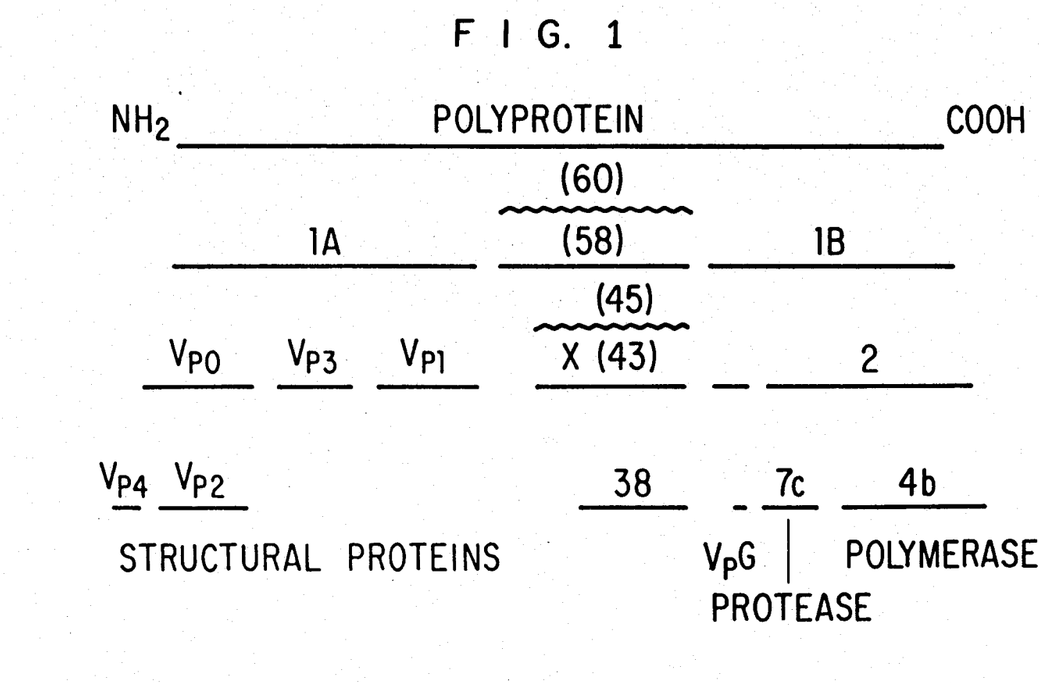
FIG. 1 is a schematic map of the RNA genome of a generalized picornavirus, indicating the relative positions of RNA domains corresponding to particular picornaviral proteins. The direction of translation is from left-to-right.
Figure 2:
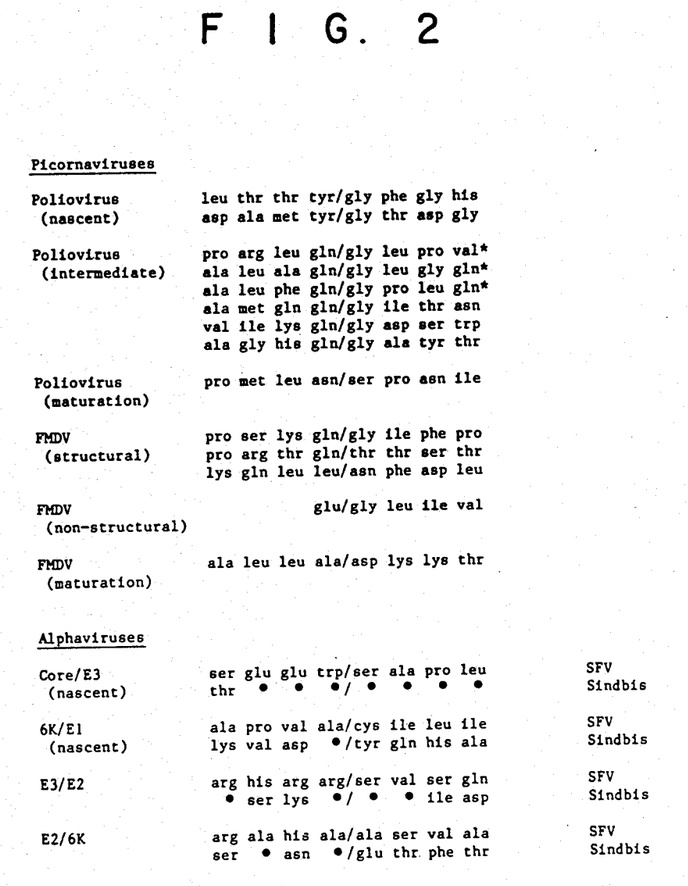
FIG. 2 is a diagram illustrating amino acid sequence homology among several known virus-specified protease cleavage recognition sites.

The homology between cleavage sites of picornavirus proteins is illustrated by FIG. 2. In FIG. 2, 22 known cleavage sites are listed, in addition to sequence information for proteins of poliovirus type 1. Cleavage sites recognized by. virus-specified proteases are indicated by a slashed line, and exact homology is indicated by filled circles. The information set forth in FIG. 2 suggests that cleavage sites for picornaviruses are frequently marked by the presence of a glutamine-glycine or glutamic acid-glycine sequences, often surrounded by hydrophobic residues such as alanine, valine, isoleucine, or leucine. Other cleavage sites which have thus far been been characterized contain an asparagine residue.

There is a greater diversity at cleavage sites of togavirus structural proteins. In the case of alphaviruses, a subset of the togavirus family, alanine residues tend to be present. Moderate to high conservation of individual sites has been observed in comparisons of Semliki Forest virus and Sindbis virus, although different sites show substantial chemical differences, suggesting participation by several proteases. All cleavages can be considered chymotryptic-like, except for a dibasic arg-arg/ser or lys-arg/ser site cleaved between envelope proteins 2 and 3.

The compounds specified by the process of the present invention can be administered alone, in combination with one another, in combination with other therapeutic agents, or in combination with various inert pharmaceutically acceptable carriers in a variety of dosage forms, orally or parenterally. Dose requirements will vary with the compound and dosage form employed and the animal being treated. Typically, therapy is initiated at lower dosages and dosage is increased until the desired inhibiting effect is achieved.

The compounds of the instant invention can be prepared by techniques generally corresponding to those disclosed by Kettner et al., *Arch. Biochem. Biophys.* 162:56 (1974), and Kettner et al., *Arch. Biochem. Biophys.* 165:739 (1974).

First, N-protected peptides or amino acids are reacted with about one equivalent of N-methylmorpholine and one equivalent of isobutyl chloroformate at about −20° C., generating a mixed peptide-isobutyric acid anhydride. This standard technique is described by Anderson et al., *J. Am. Chem. Soc.* 89:5012 (1967). Second, the resulting mixed anhydride is treated with about one equivalent of diazomethane is tetrahydrofuran or other suitable inert, aprotic solvent at 0° C., generating an N-protected peptide or amino acid diazomethyl ketone. Third, the latter compound is treated with a solution of HCl or HBr in anhydrous ethanol or ether at 0° C., producing an N-protecting halomethyl ketone. Fourth, methyl ketones can be generated from the corresponding N-protected halomethyl ketones by hydrogenolysis in anhydrous methanol, employing 10% palladium on charcoal as catalyst.

Larger peptide halomethyl ketones can be assembled by repetitively coupling a deprotected halomethyl ketone to mixed anhydrides of other N-protected peptides or amino acids generated according to the foregoing procedure. Deprotection of N-terminal amino groups can be accomplished by treatment with trifluoroacetic acid, anhydrous HF, anhydrous HCl, or by other methods known to those skilled in the art.

Corresponding peptide methyl ketones can be prepared by analogous coupling procedures in which a deprotected methyl ketone rather than a halomethyl ketone is employed. Specific examples of these procedures are disclosed below.

Generally applicable procedures suitable for producing specific peptide halomethyl ketones and methyl ketones are described in the paragraphs preceding the Examples, below. In the synthetic procedures and Examples, all parts and percentages are by weight, and all degrees are Celsius, unless otherwise noted.

GENERAL SYNTHETIC PROCEDURES

1. Mixed Anhydride Coupling Procedure (MA)

Approximately 1–2 g of an N-protected amino acid or peptide are dissolved in 20 mL of tetrahydrofuran (THF), and the resulting solution is cooled to −20°. N-methylmorpholine (1 eq) and isobutyl chloroformate (1 eq) are added and after 5 minutes, an additional 10 mL of cold THF and an equivalent of triethylamine are added. The resulting mixture is immediately added to an equivalent of an amine hydrochloride or trifluoroacetate dissolved in 5 mL of dimethylformamide (DMF). The ensuing reaction is allowed to stir 1 hour at −20° and then 2 hours at about 23°. The resulting mixture is filtered and the filtrate thereby obtained is then concentrated to approximately 5 mL by evaporation. The resulting concentrate or residue is dissolved in ethyl acetate and then washed sequentially with 0.2N hydrochloric acid, 5% sodium bicarbonate solution, and saturated aqueous sodium chloride. The resulting organic solution is then dried briefly over sodium sulfate, filtered, and finally evaporated to leave a crude peptide product.

2. N-Hydroxysuccinimide (OSu) Coupling Procedure

N-hydroxysuccinimide esters of N-protected amino acids and peptides can be prepared by procedures substantially similar to those disclosed by Anderson et al., *J. Am. Chem. Soc.* 86:1839 (1964). An OSu ester is dissolved in a minimal volume of dioxane, and the resulting solution is added to an equal volume of an aqueous solution consisting of 1.5 eq of triethylamine and either an amino acid (1.5 eq) or a peptide (1.1 eq), forming a reaction mixture. After about 5 minutes, if a complete solution is not obtained, a small test sample of the reaction mixture can be diluted with water and another sample diluted with dioxane. On the basis of the results obtained, the reaction mixture is then diluted with the appropriate solvent (either water or dioxane) until completely dissolved. After the reaction has proceeded to completion, the reaction mixture is acidified with hydrochloric acid and the resulting product extracted into ethyl acetate. The resulting extract is then washed with 0.2N hydrochloric acid followed by 0.2N hydrochloric acid in saturated sodium chloride. The washed extract is then dried over sodium sulfate, filtered, and finally evaporated to dryness to leave a crude peptide.

3. Other Coupling Procedures

Dansyl, 2,4-dinitrophenyl, and methoxysuccinyl derivatives of peptides are prepared by reacting a selected chloride, fluoride, or N-hydroxysuccinimide ester with an appropriate peptide. Acetyl and succinyl derivatives can be prepared from the corresponding anhydrides. A peptide hydrochloride or trifluoroacetate salt is dissolved in 50% aqueous dioxane at a level of 0.25 mmol/mL and the resulting solution is cooled to 0°. A selected coupling agent (1.0–1.2 eq) is dissolved in dioxane and added along with 2 eq of sodium bicarbonate. The resulting reaction is monitored by following the disappearance of ninhydrin positive material.

4. Saponification of Methyl Esters

An N-protected methyl ester is dissolved in dioxane (1 mL/mmole), and an equal volume of 1.00N sodium hydroxide is added over a period of 30 minutes. Disappearance of starting material is monitored by thin-layer chromatography. After the resulting reaction has proceeded to completion, an equivalent of 1.00N hydrochloric acid is added, and the solution is diluted to 100 mL with water. The product is then extracted into ethyl acetate, and the resulting extract washed with 0.2N hydrochloric acid followed by 0.2N hydrochloric acid in saturated sodium chloride. Solvent is then removed by evaporation to leave a crude carboxylic acid.

5. Hydrolysis of the Boc Group

Boc protecting groups are removed from peptides by dissolving a selected peptide in trifluoroacetic acid and stirring the resulting solution for 5 minutes at about 23°. Cold ether is then added. If a precipitate is obtained upon addition of ether, it is triturated with ether and isolated. If no precipitate is obtained, the ether is evaporated and toluene is added to co-evaporate residual trifluoroacetic acid, yielding the deprotected peptide as a trifluoroacetic acid salt.

Alternatively, a Boc-protected peptide can be dissolved in ethanolic hydrochloric acid (2.0–3.5N) and the resulting solution stirred at about 23° for about 30 minutes, followed by evaporation of solvent. In all cases, peptide hydrochloride or trifluoroacetate salts are dried overnight under vacuum in the presence of solid potassium hydroxide and phosphorus pentoxide.

6. Hydrolysis of t-Butyl Esters (Bu)

t-Butyl peptide esters are dissolved in trifluoroacetic acid, and the resulting solution is stirred for 1 hour at about 23°. Solvent is then evaporated, and the resulting residue is redissolved in toluene. Following a second toluene evaporation step, the remaining residue is dried in vacuo over solid potassium hydroxide. Crude product is crystallized from an appropriate solvent, e.g., toluene or ethyl acetate.

7. Thin-Layer Chromatography (TLC) Procedures

TLCs are run on 5×10 cm silica gel plates, using a fluorescent indicator. Spots are visualized by conventional techniques, using either UV light or an iodine jar. Peptides with free amino groups protected by Boc groups are exposed to HCl vapors, and then stained with ninhydrin. The following solvent systems are useful for chromatography:

methanol:chloroform (1:9)
butanol:acetic acid:water (4:1:1)
ethyl acetate:hexane (8:2)

EXAMPLE 1: Preparation and Evaluation of Peptide Halomethyl Ketones

Representative peptide halomethyl ketones were prepared by the indicated literature procedure or as described below:

A. Ac-Phe-Gly-Ala-LeuCH$_2$Cl

Ac-Phe-Gly-Ala-LeuCH$_2$Cl was prepared by condensation of N-acetyl-L-phenylalanylglycyl-L-alanine with leucine chloromethyl ketone hydrochloride using a mixed anhydride procedure employing isobutyl chloroformate. Powers et al., *Biochem. Biophys. Acta.* 480:246–261 (1977), describe an analogous procedure. Crude product was recrystallized from ethyl acetate to provide a white crystalline solid, m.p. 152.4°–153.8° (reported m.p. 167°–168°).

B. Z-Phe-Gly-Ala-LeuCH$_2$CL

A solution of 4.00 g (9.4 mmol) of Z-Phe-Gly-Ala-OH and 0.95 g of N-methylmorpholine in 100 mL of THF was cooled to −20° under nitrogen, and then 1.28 g of isobutyl chloroformate was added. After 5 minutes a solution of 1.14 g of leucine chloromethyl ketone hydrochloride in dry acetone was added, followed by 0.95 g of N-methylmorpholine. The resulting reaction mixture was stirred and allowed to warm to about 25° over a period of 2 hours. Solvent was evaporated, and the resulting residue was dissolved in ethyl acetate. This solution was washed with ice water, followed by cold 5% citric acid. The resulting solution was dried and then solvent was evaporated to leave 5.63 g of a frothy solid. This material was triturated overnight with 250 mL of ether. The resulting gel-like product was filtered from the ether and washed with additional ether, providing 3.10 g of crude product as a fine white powder. A 2.56 g portion was dissolved in 25 mL of warm ethyl acetate, forming a cloudy solution. This solution was filtered through carbon (Celite) and an additional 200 mL of ether was added. After seeding, 1.15 g of fine needle-like crystals of Z-Phe-Gly-Ala-LeuCH$_2$Cl precipitated and were collected. These crystals melted at 138°–141.8°; $\delta_D{}^{25}$ −59° (C=0.45 g/100 mL in acetone).

Anal: Calcd. for C$_{29}$H$_{37}$ClN$_4$O$_6$: C, 60.78; H, 6.51; N, 9.78; Found: C, 60.45; H, 6.44; N, 9.69.

C. Z-Phe-Gly-Leu-LeuCH$_2$Cl

As a preliminary step in synthesis of the foregoing compound, Z-Phe-Gly-Leu-OH was prepared by the following procedure.

The N-hydroxysuccinimide ester of Z-Phe-OH (19.15 g, 48.3 mmol) was dissolved in 50 mL of dioxane and the resulting solution was filtered into a solution consisting of H-Gly-Leu-OH (10.0 g, 53.1 mmol), triethylamine (10.1 mL, 72.4 mmol), and water (50 mL). This reaction mixture was stirred overnight at about 23°, and then concentrated approximately 60% by evaporation. The resulting concentrated solution was diluted with 1.0N hydrochloric acid until acidic. Product Z-Phe-Gly-Leu-OH was extracted into ethyl acetate, and the resulting extract was washed with 0.2N hydrochloric acid, followed by saturated aqueous sodium chloride adjusted to 0.10N hydrochloric acid. After washing, the ethyl acetate solution was dried over anhydrous sodium sulfate and filtered. The ethyl acetate was then evaporated to yield 22.5 g of a white, foamy product, which was subsequently crystallized from ethyl acetate to yield 16.7 g of Z-Phe-Gly-Leu-OH (m.p. 147°–148°).

Anal: Calcd. for C$_{25}$H$_{31}$N$_3$O$_6$: C, 63.94; H, 6.67; N, 8.95; Found: C, 64.19; H, 6.65; N, 8.90.

H-LeuCH$_2$Cl.HCl was prepared substantially according to the procedure disclosed by Kettner et al., *Arch. Biochem. Biophys.* 165:739–743 (1974).

A mixed anhydride was prepared by dissolving Z-Phe-Gly-Leu-OH (1.05 g, 2.24 mmol) in 10 mL of tetrahydrofuran, cooling the resulting solution to −20°, and adding N-methylmorpholine (0.25 mL, 2.24 mmol) and isobutyl chloroformate (0.29 mL, 2.24 mmol). The resulting mixture was stirred for 5 minutes at −20°, and then 20 mL of cold tetrahydrofuran and triethylamine (0.31 mL, 2.24 mmol) were added. This mixture was added to a solution of H-LeuCH$_2$Cl.HCl (0.48 g, 2.24 mmol) in 5 mL cold N,N-dimethylformamide. The resulting reaction mixture was stirred for about 1 hour at −20°, and then for 2 hours at about 23°. The mixture was then filtered, and tetrahydrofuran evaporated from the filtrate. The resulting residue was dissolved in 100 mL of ethyl acetate. This solution was then sequentially washed with 0.2N hydrochloric acid, 5% aqueous sodium bicarbonate, and saturated aqueous sodium chloride. The washed extract was then dried over anhydrous sodium sulfate and then solvent was evaporated to yield 1.2 g of a foam. This product was crystallized from ethyl acetate to yield 0.94 g (m.p. 160°–161.5°) of Z-Phe-Gly-Leu-LeuCH$_2$Cl.

Anal: Calcd. for C$_{32}$H$_{43}$N$_4$O$_6$Cl: C, 62.47; H, 7.06; N, 9.11; Found: C, 62.32; H, 6.90; N, 9.14.

D. Z-Phe-Gly-Ala-LeuCH$_2$Br

A mixed anhydride of Z-Phe-Gly-Ala-OH (0.41 g, 0.95 mmol) was prepared and coupled to H-LeuCH$_2$Br.HBR substantially according to the procedure described for preparation of Z-Phe-Gly-Leu-LeuCH$_2$Cl, above. The resulting product was crystallized from ethyl acetate:hexane to yield 0.30 g. Product was recrystallized from the same solvents to yield 0.07 g, m.p. 135.5°–138° (dec.).

Anal. Calcd. for C$_{29}$H$_{37}$N$_4$O$_6$Br: C, 56.39; H, 6.05; N, 9.07; Found: C, 56.70; H, 6.26; N, 8.97.

E. Z-Phe-Gly-Ala-ValCH$_2$Cl

First, precursor H-ValCH$_2$Cl.HCl was prepared by dissolving Boc-Val-OH (6.5 g, 30 mmol) in 10 mL of THF and treating it with N-methylmorpholine (3.3 mL, 30 mmol) and isobutyl chloroformate (3.9 mL, 30 mmol) for 10 minutes at −20°. The resulting mixture was filtered and the retained material was washed with 40 mL of cold THF. The combined filtrates were added to 200 mL of diazomethane:ether. The resulting solution was stirred for 2 hours at 0°, and then solvent was removed by evaporation to yield an oil. The oil was dissolved in ethyl acetate, washed with 5% sodium bicarbonate followed by saturated aqueous sodium chloride, and then dried over sodium sulfate. Evaporation of solvent left 6.4 g of an oil. The oil was dissolved in 100 mL of ether, and the resulting solution was treated with a 5% excess of ethanolic HCl for 15 minutes at 0°. This solution was washed with cold water followed by saturated aqueous sodium chloride, and then dried over sodium sulfate. After evaporation of solvent, product was washed with hexane to yield 2.7 g of Boc-ValCH$_2$Cl (m.p. 70°–73°). Boc-ValCH$_2$Cl (1.0 g) was deblocked by stirring with 5 mL of 3N ethanolic HCl for 30 minutes at about 23°. Solvent was evaporated and the resulting residue was triturated with ether to yield 0.69 g of H-ValCH$_2$Cl.HCl.

Z-Phe-Gly-Ala-OH (1.60 g, 3.73 mmol) was then coupled to H-ValCH$_2$Cl.HCl by a procedure substantially similar to that described for the preparation of Z-Phe-Gly-Leu-LeuCH$_2$Cl, above. The resulting product was crystallized from ethyl acetate:ether to yield 1.29 g of Z-Phe-Gly-Ala-ValCH$_2$Cl (m.p. 143°–144°).

Anal: Calcd. for C$_{28}$H$_{35}$N$_4$O$_6$Cl: C, 60.14; H, 6.32; N, 10.02; Found: C, 59.92; H, 6.25; N, 10.05.

F. Z-Phe-Gly-Ala-TyrCH$_2$Cl

Boc-TyrCHN$_2$ was prepared by dissolving Boc-Tyr-OH (10 g, 35.5 mmol) in 30 mL of tetrahydrofuran and then reacting it with N-methylmorpholine (3.91 mL, 35.5 mmol) and isobutyl chloroformate (4.62 mL, 35.5 mmol) for 5 minutes at −20°. The resulting reaction mixture was filtered, and the material retained by the filter was washed with 50 mL of cold tetrahydrofuran. The resulting filtrates were collected and combined. The combined filtrates were added to 150 mL of diazomethane:ether (~40 mmol) and the resulting reaction mixture was stirred for 15 minutes at 0°. Solvent was then evaporated with a stream of nitrogen. The remaining residue was dissolved in ethyl acetate and the resulting solution was washed with water followed by saturated aqueous sodium chloride. The washed solution was then dried over sodium sulfate, and then solvent was evaporated to yield a crude product. This material was chromatographed on a 4 cm column containing 75 g of silica gel, using chloroform as a solvent, to yield 3.67 g of Boc-TyrCHN$_2$. This product crystallized from ether to yield 1.86 g (m.p. 136°–137°) in a first crop, and 0.58 g (m.p. 133.5°–134.5°) in a second crop. NMR in CDCl$_3$ indicated a diazo proton at δ5.27.

Anal: Calcd. for C$_{15}$H$_{19}$N$_3$O$_4$: C, 58.99; H, 6.28; N, 13.76; Found: C, 59.08; H, 6.16; N, 13.65.

Boc-TyrCHN$_2$ (1.81 g, 5.92 mmol) was dissolved in 30 mL of tetrahydrofuran, and the resulting solution was treated with 3.45N ethanolic:HCl (1.72 mL, 5.92 mmol) for 5 minutes at 0°. Solvent was removed by evaporation on a rotary evaporator without temperature regulation. The remaining residue was dissolved in ethyl acetate, and the resulting solution was washed with 0.2N hydrochloric acid followed by saturated aqueous sodium chloride. The washed solution was dried over sodium sulfate, and then solvent was evaporated to yield crystalline Boc-TyrCH$_2$Cl. Crystals were isolated and washed with cold ether to yield 0.45 g (m.p. 110°–112°) in a first crop, and 0.90 g (m.p. 110°–112°) in a second crop. NMR spectra in CDCl$_3$ corresponded to that expected, except that methylene protons of —COCH$_2$Cl appeared as a doublet at δ4.1.

Anal: Calcd. for C$_{15}$H$_{20}$NO$_4$Cl: C, 57.41, H, 6.44; N, 4.46; Found: C, 57.66; H, 6.66; N, 4.52.

Boc-TyrCH$_2$Cl (0.5 g) was deblocked by treatment with 20 mL of 3.5N ethanolic HCl for 30 minutes at about 23°. Solvent was evaporated and the resulting product, H-TyrCH$_2$Cl.HCl (0.45 g), was dried in vacuo over solid potassium hydroxide and phosphorus pentoxide.

Z-Phe-Gly-Ala-OH (0.77 g, 1.80 mmol) was coupled to H-TyrCH$_2$Cl.HCl by a mixed anhydride coupling procedure substantially similar to that described for preparation of Z-Phe-Gly-Leu-LeuCH$_2$Cl in Procedure C, above. Product was crystallized from ethyl acetate to yield 0.73 g of Z-Phe-Gly-Ala-TyrCH$_2$Cl. Product slowly decomposed at 140°–160° and melted with complete decomposition at 160°–160.5°.

Anal: Calcd. for C$_{32}$H$_{35}$N$_4$O$_7$Cl: C, 61.67; H, 5.67; N, 8.99; Found: C, 61.60; H, 5.92; N, 8.69.

G. MeOSuc-Phe-Gly-Leu-LeuCH$_2$Cl

MeOSuc-Phe-Gly-Leu-OH was prepared from Z-Phe-Gly-Leu-OH, as described above in Procedure C. Z-Phe-Gly-Leu-OH (4.00 g, 8.52 mmol) was dissolved in 100 mL of methanol and hydrogenated in the presence of 1.0 eq of anhydrous HCl and 0.50 g of 10% Pd on carbon overnight in a Parr apparatus. The resulting reaction mixture was filtered and solvent was evaporated to yield 3.1 g of H-Phe-Gly-Leu-OH as a foam.

This product was dissolved in 5 mL of N,N-dimethylformamide, to which N-hydroxysuccinimide ester of methoxysuccinic acid (1.9 g, 8.4 mmol) and triethylamine (1.2 mL, 8.4 mmol) were added. This reaction mixture was stirred for 0.50 hr at ambient temperature, then additional triethylamine (0.58 mL, 4.2 mmol) was added. The reaction mixture was then stirred overnight. At this point, 5 mL of a 5% solution of aqueous sodium bicarbonate was added. After 5 min, the reaction mixture was diluted to 50 mL with 5% aqueous sodium bicarbonate to yield a precipitate, which was discarded. Ethyl acetate was added to the reaction mixture to extract product MeOSuc-Phe-Gly-Leu-OH. The aqueous portion of the resulting extraction mixture was acidified with hydrochloric acid, and then the ethyl acetate phase or extract was separated from the aqueous portion. The extract was washed with 0.20N hydrochloric acid, followed by saturated sodium chloride prepared in 0.20N hydrochloric acid. The washed solution was then dried over sodium sulfate. Solvent was evaporated and the resulting residue was crystallized from ethyl acetate, yielding 1.30 g of MeOSuc-Phe-Gly-Leu-OH (m.p. 167.5°–168.5°).

Anal: Calcd. for C$_{23}$H$_{32}$N$_3$O$_7$: C, 58.91; H, 6.76; N, 9.37; Found: C, 59.20; H, 6.99; N, 9.06.

MeOSuc-Phe-Gly-Leu-OH (1.0 g, 2.23 mmol) was coupled to H-LeuCH$_2$Cl.HCl by a procedure substantially similar to that described for preparation of Z-Phe-Gly-Leu-LeuCH$_2$Cl. After coupling, solvent was evaporated to yield a foamy product which crystallized from ethyl acetate, providing 0.30 1 g (m.p. 116°–117°) of MeOSuc-Phe-Gly-Leu-LeuCH$_2$Cl in a first crop and 0.25 g (m.p.115°–116°) in a second crop. A sample of the first crop was analyzed.

Anal: Calcd. for C$_{29}$H$_{43}$N$_4$O$_7$Cl: C, 58.51; H, 7.30; N, 9.42; Found: C, 58.67; H, 7.20; N, 9.31.

H. Suc-Phe-Gly-Ala-LeuCH$_2$Cl

Boc-Phe-Gly-Ala-Oh was prepared substantially according to the mixed anhydride coupling procedure described previously, except amine components were added in tetrahydrofuran or tetrahydrofuran containing the minimum quantity of water needed to dissolve the amine hydrochlorides. Methyl esters were saponified with aqueous sodium hydroxide in methanol.

Boc-Gly-Ala-OCH$_3$ was prepared by coupling Boc-Gly-OH (35.0 g, 200 mmol) to H-Ala-OCH$_3$.HCl (27.9 g, 200 mmol) using a mixed anhydride procedure. The resulting product (43.5 g, 167 mmol) was deblocked with anhydrous HCl in dioxane. After deblocking, crystallization from dioxane:ether yielded 27.1 g of H-Gly-Ala-OCH$_3$.HCl.

Boc-Phe-OH (26.5 g, 100 mmol) was coupled to H-Gly-Ala-OCH$_3$.HCl (19.6 g, 100 mmol) using a mixed anhydride procedure. After crystallization from ethyl acetate:hexane, 30.2 g of Boc-Phe-Gly-Ala-OCH$_3$ (m.p. 126.4°–127.8°) were obtained.

Anal: Calcd. for C$_{20}$H$_{29}$N$_3$O$_6$: C, 58.95; H, 7.71; N, 10.31; Found: C, 59.49; H, 7.05; N, 10.26.

Boc-Phe-Gly-Ala-OCH$_3$ (28.4 g, 69.7 mmol) was saponified to yield 22 g of solid Boc-Phe-Gly-Ala-OH. It was crystallized from acetone:ether to yield 20 g of product (m.p. 105.7°–109°).

Anal: Calcd. for C$_{19}$H$_{27}$N$_3$O$_6$: C, 58.00; H, 6.92; N, 10.68; Found: C, 58.04; H, 6.78; N, 10.66.

Boc-Phe-Gly-Ala-LeuCh$_2$Cl was prepared by coupling Boc-Phe-Gly-Ala-OH (11.8 g, 30 mmol) to H-LeuCH$_2$Cl.HCl (6.06 g, 30 mmol) using a mixed anhydride procedure. A mixed anhydride of Boc-Phe-Gly-Ala-OH was prepared in a solution of 300 mL of tetrahydrofuran and 25 mL of acetone, and then H-LeuCH$_2$Cl.HCl was added in acetone. The resulting crude product, 17.6 g, was dissolved in ether, treated with carbon, and filtered. Product Boc-Phe-Gly-Ala-LeuCH$_2$Cl crystallized from ether (10.0 g).

Anal: Calcd. for C$_{20}$H$_{39}$N$_4$O$_6$Cl: C, 57.93; H, 7.29; N, 10.39; Found: C, 57.92; H, 7.53; N, 10.17.

Boc-Phe-Gly-Ala-LeuCH$_2$Cl (0.30 g) was treated with 1 ml of anhydrous trifluoroacetic acid for 5 minutes at about 230°, forming trifluoroacetate salt, which was precipitated by addition of cold ether and then washed with additional cold ether. The salt was then dried over solid potassium hydroxide and phosphorus pentoxide to yield 0.31 g (0.55 mmole) of H-Phe-Gly-Ala-LeuCH$_2$Cl trifluoroacetate. This product was dissolved in 2 mL of 50% dioxane:water, and the resulting solution was cooled to 0°. Sodium bicarbonate (0.09 g, 1.11 mmol) and succinic anhydride (0.066 g, 0.66 mmol) dissolved in 1 mL of dioxane were added. After 1 hour, 0.55 mL of 1.0N hydrochloric acid was added, and the resulting solution was diluted to 10 mL with water and held overnight at 4°. During this period product Suc-Phe-Gly-Ala-LeuCH$_2$Cl crystallized from solution. This product was filtered and washed with 100 mL of cold 0.10N hydrochloric acid. After drying in vacuo, 0.18 g of Suc-Phe-Gly-Ala-LeuCH$_2$Cl (m.p. 157.5°–158°) was obtained.

Anal: Calcd. for C$_{25}$H$_{35}$N$_4$O$_7$Cl: C, 55.70; H, 6.56; N, 10.40; Found: C, 55.47; H, 6.59; N, 10.48.

I. MeOSuc-Phe-Gly-Ala-LeuCH$_2$Cl

Suc-Phe-Gly-Ala-LeuCH$_2$Cl (0.20 g, 0.37 mmole) was dissolved in 10 mL of acetone, and the resulting solution was treated with diazomethane:ether (10 mL) for 30 minutes at 0°. Solvent was evaporated after the solution was warmed to about 23°. The remaining residue was dissolved in acetone, and the resulting solution was filtered and concentrated by evaporation of solvent. The concentrate was diluted with ethyl acetate, and this solution was again concentrated by evaporation to remove most of the acetone. A crystalline product separated. This product was isolated and washed with cold ethyl acetate to yield 0.11 g of MeOSuc-Phe-Gly-Ala-LeuCH$_2$Cl (m.p. 128.5°–129.5°).

Anal: Calcd. for C$_{26}$H$_{37}$N$_4$O$_7$Cl: C, 56.45; H, 6.76; N, 10.13; Found: C, 56.26; H, 6.69; N, 10.01.

J. Boc-Gly-Ala-LeuCH$_2$Cl

Boc-Gly-Ala-OH was prepared by an N-hydroxysuccinimide coupling procedure. Boc-Gly-OSu (7.67 g, 28.2 mmol) was dissolved in 10 mL of dimethylsulfoxide and the resulting solution was added to a solution consisting of H-Ala-OH (3.76 g, 42.3 mmol) and triethylamine (5.89 mL, 42.3 mmol) in 20 mL of water. After stirring overnight, a precipitate was removed by filtration. The remaining solution was diluted with water and then acidified with hydrochloric acid. An aqueous phase separated from which product was extracted by addition of ethyl acetate. The ethyl acetate extract was washed with 0.2N hydrochloric acid and then saturated sodium chloride prepared in 0.2N hydrochloric acid. The washed ethyl acetate solution was then dried over sodium sulfate and filtered. Solvent was then evaporated, leaving a foamy product, which was crystallized from ethyl acetate:hexane to yield 2.88 g of Boc-Gly-Ala-OH (m.p. 128°–130°).

Anal: Calcd. for C$_{10}$H$_{18}$N$_2$O$_5$: C, 48.76; H, 7.38; N, 11.38; Found: C, 49.12; H, 7.27; N, 11.28.

Boc-Gly-Ala-OH (2.5 g, 10.2 mmol) was coupled to H-LeuCH$_2$Cl.HCl by a procedure substantially similar to that described for the preparation of Z-Phe-Gly-Leu-LeuCH$_2$Cl. Evaporation of ethyl acetate provided 3.7 g of a foam. Crystallization from ethyl acetate:hexane gave 3.1 g of Boc-Gly-Ala-LeuCH$_2$Cl (m.p. 95°–99.5°).

Anal: Calcd. for C$_{17}$H$_{30}$N$_3$O$_5$Cl: C, 52.09; H, 7.73; N, 10.72; Found: C, 52.21; H, 7.46; N, 10.63.

K. Z-Phe-Ser-Ala-LeuCH$_2$Cl

Z-Phe-Ser(OCH$_2$C$_6$H$_5$)-Ala-OH was prepared according to the following mixed anhydride coupling procedure.

First, Boc-Ser(OCH$_2$C$_6$H$_5$)-OH (4.93 g, 16.7 mmol) was coupled to H-Ala-OCH$_3$.HCl (2.80 g, 20.0 mmol) by a mixed anhydride procedure to yield an oil, 6.1 g. Boc-Ser(OCH$_2$C$_6$H$_5$)-Ala-OCH$_3$ was then deblocked with trifluoroacetic acid, and the resulting product, H-Ser(OCH$_2$C$_6$H$_5$)-Ala-OCH$_3$ trifluoroacetate (6.15 g, 15.6 mmol), was coupled to Z-Phe-OH (3.89 g, 13.0 mmol) using a mixed anhydride procedure. This product was crystallized from ethyl acetate to yield 5.4 g of Z-Phe-Ser(OCH$_2$C$_6$H$_5$)-Ala-OCH$_3$ (m.p. 158°–159°).

Anal: Calcd. for C$_{31}$H$_{35}$N$_3$O$_7$: C, 66.28; H, 6.29; N, 7.48; Found: C, 65.54; H, 6.24; N, 7.37.

Z-Phe-Ser(OCH$_2$C$_6$H$_5$)-Ala-OCH$_3$ (4.63 g, 8.24 mmol) was saponified substantially as previously described, except that 16 mL of dioxane and 8.25 mL of 1.00N sodium hydroxide were used. The desired product, Z-Phe-Ser(OCH$_2$C$_6$H$_5$)-Ala-OH, crystallized from methanol:ethyl acetate to yield 3.5 g (m.p. 171.5°–172.5°).

Anal: Calcd. for C$_{30}$H$_{33}$N$_3$O$_7$: C, 65.79; H, 6.08; N, 7.67; Found: C, 65.50; H, 5.86; N, 7.84.

Z-Phe-Ser(OCH$_2$C$_6$H$_5$)-Ala-LeuCH$_2$Cl was prepared by coupling Z-Phe-Ser(OCH$_2$C$_6$H$_5$)-Ala-OH (1.37 g, 2.5 mmol) to H-LeuCH$_2$Cl.HCl by a mixed anhydride coupling procedure substantially similar to that used for the preparation of Z-Phe-Gly-Leu-LeuCH$_2$Cl in Procedure C, above. Product was obtained as a crystalline solid, 0.98 g (m.p. 167°–168°).

Anal: Calcd. for $C_{37}H_{45}N_4O_7$: C, 64.09; H, 6.56; N, 8.08; Found: C, 64.22; H, 6.38; N, 8.08.

Z-Phe-Ser(OCH$_2$C$_6$H$_5$)-Ala-LeuCH$_2$Cl (0.71 g, 10.2 mmol) was treated with a mixture of 15 mL of anhydrous HF and 1 mL of anisole in a commercial HF apparatus (Peptide Institute, Inc.) After 70 minutes at 0°, HF was removed by evaporation, leaving a residue which was dried in vacuo over potassium hydroxide overnight. H-Phe-Ser-Ala-LeuCH$_2$Cl.HF, 0.35 g, was obtained after triturating the residue with ether.

This hydrofluoride salt (0.39 g, 0.71 mmole) was dissolved in a mixture of 2 mL water and 1 mL of dioxane. The resulting solution was cooled to 0° and carbobenzoxychloride (0.10 mL, 0.71 mmole) and sodium bicarbonate (0.12 g, 1.42 mmol) were added. After 30 minutes at 0°, no ninhydrin positive material could be detected. The resulting reaction mixture was diluted with ethyl acetate and the resulting organic layer was washed sequentially with 5% sodium bicarbonate solution, 0.2N hydrochloric acid, and saturated sodium chloride. The washed solution was dried over sodium sulfate and solvent was evaporated, leaving a residue, which was diluted by 50% with hexane to yield 0.13 g of Z-Phe-Ser-Ala-LeuCH$_2$Cl (m.p. 155°–157°).

Anal. Calcd. for $C_{30}H_{39}N_4O_7Cl$: C, 59.73; H, 6.53; N, 9.29; Found: C, 59.81; H, 6.47; N, 9.13.

L. Z-Phe-Gly-Ser-LeuCH$_2$Cl

Z-Phe-Gly-Ser-LeuCH$_2$Cl was prepared by the following procedure. First, Z-Phe-Gly-Ser(OCH$_2$C$_6$H$_4$)LeuCH$_2$Cl (0.98 g, 14.4 mmol) was deblocked by treatment with 15 mL of anhydrous HF and 1 mL of anisole (Procedure K) to yield 0.69 g of H-Phe-Gly-Ser-LeuCH$_2$Cl.HF. This intermediate (0.59 g, 12.4 mmol) was then coupled with carbobenzoxychloride substantially according to the procedure of Procedure K to yield 0.4 g of Z-Phe-Gly-Ser-LeuCH$_2$Cl (m.p. 146°–146.5°) after crystallization from ethyl acetate/hexane.

Anal: Calcd. for $C_{29}H_{37}N_4O_7Cl$: C, 59.12; H, 6.34; N, 9.51; Found: C, 59.45; H, 6.37; N, 9.46.

Biological Activity of Selected Peptide Halomethyl Ketones

Selected compounds have been shown to inhibit viral protease activity in two assays. One assay, known as a viral cleavage assay, involves comparison of patterns of proteins synthesis (as visualized by incorporation of labeled amino acids) in virus-infected HeLa cells grown in the presence and absence of a selected test compound. A second assay, known as a plaque inhibition assay, involves an assessment of the effects of test compounds upon the infectivity of virus in agar-overlaid cell cultures. Toxic effects of a test compound, if any, will also be observed during the incubation period of the plaque inhibition assay. Both assays are described in greater detail below.

Viral Cleavage Assay

In this assay, samples of growing HeLa-O cells were exposed to human poliomyelitisvirus type 2 or human rhinovirus type 1A at a virus concentration of about 10 infectious virus particles per cell. After several hours, host cell metabolism was markedly inhibited, and added radioactive amino acids were incorporated into viral proteins only. After varying concentrations of a test compound were added to cell samples, viral proteins were labeled for 60 minutes at the mid-cycle of infection (3–5 hours after first exposure of the cells to the virus).

Cell samples were then solubilized in 0.01M tris(hydroxymethyl)aminomethane buffer, pH 6.8, containing 1% (w/v) sodium dodecyl sulfate and 1% (v/v) 2-mercaptoethanol. The resulting labeled viral proteins were separated on a polyacrylamide gel and detected by autoradiography, as previously described by Korant et al., *Proc. Natl. Acad. Sci. USA* 76: 2992 (1979). If a selected concentration of the test compound disrupted the usual pattern of virus protein processing, that compound was scored as active at that concentration. Gels corresponding to cell samples labeled in the presence of test compounds exhibiting viral protease-inhibiting activity were generally distinguishable by appearance of high molecular weight protein species not apparent on control gels.

Plaque Inhibition Assay

In this assay, cultured HeLa cells were grown to confluency in 60 mm plastic petri dishes. Each culture was then infected with approximately 300 plaque-forming units of virus. Human rhinovirus type 1A was used in the test reported below. The virus employed in this experiment was allowed to absorb to the cells for 30 minutes at 34.5°.

The compound tested was dissolved in ethanol at a concentration 100 times greater than the highest concentration to be tested. The resulting solution was then diluted 1:100 into a solution of McCoy's medium containing 5% heat-inactivated fetal calf serum and 0.38% agar. Two-fold dilutions were then made into agar medium.

After virus adsorbed to the cells, excess virus was washed away and each culture was overlaid with 5 mL of agar medium containing a pre-selected dilution of the compound to be tested. Controls were overlaid with agar medium only. Each culture was then incubated at 34.5° to allow development of plaques.

A plaque is a roughly circular region of dead cells in a culture, indicating an area where one plaque-forming unit of virus first infected one cell. The agar overlay restricts virus mobility, so that viral infection is communicated only between contiguous cells.

When plaques in control cultures were large enough to be observed, yet still relatively discrete, all cultures were stained with 1% crystal violet. Plaques appeared as clear areas in a deep purple field of uninfected cells. Toxic doses of the test compound resulted in visible cell detachment in culture dishes.

Protease-Inhibiting Activity of Peptide Halomethyl Ketones in Viral Cleavage Assay The results obtained in a series of experiments in which representative tetrapeptide and tripeptide chloromethyl ketones were tested for protease-inhibiting activity in the viral cleavage assay using poliovirus are set forth in Tables 1 and 2, below. The resuls are scored as follows:

| | |
|---|---|
| − | no activity |
| +/− | low activity |
| + | active at 100 µg/mL |
| ++ | active at 50 µg/mL |
| +++ | active at 10 µg/mL |
| ++++ | active at <5 µg/mL |

TABLE 1

Protease-Inhibiting Activity of Selected
Peptide Halomethyl Ketones

| Test | Peptide Analog | Activity |
|---|---|---|
| 1 | Z—Phe—Gly—Ala—LeuCH$_2$Cl | +++ |
| 2 | Ac—Phe—Gly—Ala—LeuCH$_2$Cl | +++ |
| 3 | Suc—Phe—Gly—Ala—LeuCH$_2$Cl | +++ |
| 4 | MeOSuc—Phe—Gly—Ala—LeuCH$_2$Cl | +++ |
| 5 | DNS—Phe—Gly—Ala—LeuCH$_2$Cl | +++ |
| 6 | DNP—Phe—Gly—Ala—LeuCH$_2$Cl | +++ |
| 7 | Boc—Gly—Ala—LeuCH$_2$Cl | ++ |
| 8 | Z—Leu—Gly—Ala—LeuCH$_2$Cl | +++ |
| 9 | Z—Phe—Gly—Gly—LeuCH$_2$Cl | +++ |
| 10 | Z—Phe—Gly—Ala—LeuCH$_2$Br | +++ |
| 11 | Z—Phe—Gly—Ala—ValCH$_2$Cl | ++ |
| 12 | Z—Phe—Gly—Leu—LeuCH$_2$Cl | ++++ |
| 13 | Z—Phe—Leu—Ala—LeuCH$_2$Cl | ++ |
| 14 | Z—Phe—Gly—Phe—LeuCH$_2$Cl | ++ |
| 15 | Z—Phe—Gly—Ser—LeuCH$_2$Cl | ++ |
| 16 | Z—Phe—Gly—Pro—LeuCH$_2$Cl | ++ |
| 17 | MeOSuc—Ala—Ile—Phe—LeuCH$_2$Cl | +++ |
| 18 | MeOSuc—Phe—Gly—Leu—Glu(OCH$_3$)CH$_2$Cl | ++++ |
| 19 | MeOSuc—Ala—Ile—Phe—Glu(OCH$_3$)CH$_2$Cl | +++ |
| 20 | Z—Phe—Gly—Ala—TyrCH$_2$Cl | ++ |

TABLE 2

Comparative Experiments Involving
Other Peptide Halomethyl Ketones

| Comparison | Peptide Analog | Activity |
|---|---|---|
| A | H—Phe—Gly—Ala—LeuCH$_2$Cl | +/− |
| B | Z—Ala—Gly—Ala—LeuCH$_2$Cl | +/− |
| C | Z—Gln—Gly—Ala—LeuCH$_2$Cl | + |
| D | Z—Phe—Phe—Ala—LeuCH$_2$Cl | +/− |
| E | Z—Phe—Ser—Ala—LeuCH$_2$Cl | + |
| F | Z—Phe—Gly—Lys—LeuCH$_2$Cl | + |
| G | Z—Phe—Lys—Ala—LeuCH$_2$Cl | + |
| H | Z—Phe—Pro—Ala—LeuCH$_2$Cl | + |
| I | Ac—Phe—Gly—Glu—LeuCH$_2$Cl | +/− |
| J | Ac—Phe—Glu(OEt)—Ala—LeuCH$_2$Cl | +/− |
| K | Ac—Phe—Glu—Ala—LeuCH$_2$Cl | +/− |

The antiviral activity of Z-Phe-Gly-Leu-LeuCH$_2$Cl on rhinovirus type 1A was evaluated by a plaque inhibition assay as described above. Antiviral activity, as scored by 90% plaque reduction, was noted at 1 μg/mL, whereas cytotoxicity was first detected at a concentration of about 15 μg/mL with human HeLa-O cells.

EXAMPLE 2: Preparation and Testing of Selected Peptide Methyl Ketones

A. Z-Phe-Gly-Ala-LeuCH$_3$

H-LeuCH$_3$.HBr was prepared by a procedure substantially similar to that disclosed by Kettner et al., Arch. Biochem. Biophys. 165: 739 (1974). Z-Phe-Gly-Ala-OH was prepared according to the following procedure. An N-hydroxysuccinimide ester of Z-Phe-OH was dissolved in dioxane, and the resulting solution filtered into a solution contaning about one equivalent of H-Gly-Ala-OH, about 1.5 equivalents triethylamine, and water. The resulting reaction mixture was stirred overnight at about 23°, and then concentrated to approximately 60% of its original volume by evaporation. This concentrated solution was then diluted with 1.0N hydrochloric acid until acidic. The resulting product was extracted into ethyl acetate, and the resulting extract washed with 0.2N hydrochloric acid followed by saturated aqueous sodium chloride adjusted to 0.1N hydrochloric acid. The washed extract was then dried over anhydrous sodium sulfate and filtered. Solvent was then evaporated from the extract to provide product Z-Phe-Gly-Ala-OH as a foam. This crude product was recrystallized from ethyl acetate.

Z-Phe-Gly-Ala-OH was coupled to H-LeuCH$_3$.HBr as follows. First, a mixed anhydride of Z-Phe-Gly-Ala-OH was prepared by dissolving Z-Phe-Gly-Ala-OH (1.22 g, 2.85 mmol) and N-methylmorpholine (0.32 mL, 2.85 mmol) in 35 mL tetrahydrofuran. The resulting solution was cooled to about −20°, and 0.25 mL (1.90 mmol) isobutyl chloroformate was added. After 10 minutes, the resulting solution was added to H-LeuCH$_2$.HBr (0.40 g, 1.90 mmol) dissolved in 5 mL cold dimethylformamide containing 0.26 mL (1.90 mmol) triethylamine. The resulting mixture was stirred for 1 hour at −20°, allowed to warm to about 23°, and then stirred overnight at about 23°. The resulting solution was filtered , and then evaporated to a volume of about 5 mL. 100 mL ethyl acetate was added and the resulting solution was washed sequentially with 5% sodium bicarbonate, 0.2N hydrochloric acid, and saturated aqueous sodium chloride. After drying over sodium sulfate and filtering to remove undissolved material, solvent was removed by evaporation to yield 0.88 g of a white solid, which was recrystallized from hot ethyl acetate to provide a first crop (0.27 g, m.p. 133°–134°) and a second crop (0.25 g. m.p. 133.5°–134°). Thin layer chromatography in MeOH:CHCl$_3$ (1:9, V:V) indicated a single spot, Rf 0.48. NMR spectra were consistent with predicted structure.

Anal: Calcd. for C$_{29}$H$_{38}$N$_4$O$_6$: C, 64.65; H, 7.12; N, 10.40. Found: C, 64.51; H, 6.91; N, 10.56.

B. MeOSuc-Phe-Gly-Leu-LeuCHhd 3

Z-Phe-Gly-Leu-LeuCH$_3$ was prepared by coupling Z-Phe-Gly-Leu-OH (2.23 g. 4.76 mmol) to H-LeuCH$_3$.HBr by a procedure substantially similar to that described for preparation of Z-Phe-Gly-Ala-LeuCH$_3$, above. Product was recrystallized from ethyl acetate to yield 2.34 g of Z-Phe-Gly-Leu-LeuCH$_3$ (m.p. 165.5°–166.5°).

Anal: Calcd. for C$_{32}$H$_{44}$N$_4$O$_6$: C, 66.26; H, 7.66; N, 9.66. Found: C, 66.48; H, 7.75; N, 9.66.

Z-Phe-Gly-Leu-LeuCH$_3$ (1.0 g, 1.72 mmol) was dissolved in 100 mL of absolute ethanol to which 0.5 g of 10% palladium on carbon and 0.5 mL of 4N ethanolic HCl were added. The resulting mixture was hydrogenated at an initial pressure of 40 psi (276 kPa) overnight. Catalyst was removed by filtration, and then solvent was evaporated to yield a foam, 0.85 g, which solidified after addition of ether. This product was extensively washed with ether and dried in vacuo over solid potassium hydroxide and phosphorus pentoxide.

H-Phe-Gly-Leu-LeuCH$_3$.HCl (0.62 g. 1.29 mmol) and the N-hydroxysuccinimide ester of methyl succinate (0.30 g. 1.29 mmol) were dissolved in 5 mL of N,N-dimethylformamide, and then triethylamine (0.18 mL, 1.29 mmol) was added. After stirring overnight, 5 mL of 5% aqueous sodium bicarbonate were added, and the resulting solution was stirred for 15 minutes. The resulting product was extracted into ethyl acetate. The extract was washed sequentially with 5% aqueous sodium bicarbonate, 0.2N hydrochloric acid, and saturated aqueous sodium chloride. The washed extract was dried over anhydrous sodium sulfate and filtered. Solvent was then evaporated to yield product as an oil. Product crystallized from ethyl acetate:hexane to yield 0.68 g of MeOSuc-Phe-Gly-Leu-LeuCH$_3$ (m.p. 113.5°–114°).

Anal: Calcd. for C$_{29}$H$_{41}$N$_4$O$_7$: C, 62.45; H, 7.42; N, 10.05. Found: C, 62.09; H, 7.82; N, 10.10.

Biological Activity of Selected Tetrapeptide Methyl Ketones

Selected tetrapeptide methyl ketones have been shown to inhibit viral protease activity in the viral cleavage assay and the plaque inhibition assay. These assays were conducted substantially as perviously described.

Assay of Tetrapeptide Methyl Ketones for Viral Protease-Inhibiting Activity in Viral Cleavage Assay The following compounds demonstrated activity in the viral cleavage assay against poliovirus type 2 and rhinovirus type 1A at a test concentration of 100 μg/mL. The compounds Z-Phe-Gly-Ala-LeuCH$_3$ and MeOSuc-Phe-Gly-Leu-LeuCH$_3$ were also active at 50 μg/mL against poliovirus type 2. The compound Boc-Phe-Gly-Ala-LeuCH$_3$ failed to show activity in this assay.

| Test | Compound |
|---|---|
| 1 | Z—Phe—Gly—Ala—LeuCH$_3$ |
| 2 | MeOSuc—Phe—Gly—Ala—LeuCH$_3$ |
| 3 | Z—Phe—Gly—Leu—LeuCH$_3$ |

Assay of Z-Phe-Gly-Ala-LeuCH$_3$ for Antiviral Activity in Plaque Inhibition Assay The compound Z-Phe-Gly-Ala-LeuCH$_3$ provided plaque reduction in excess of 90% with both poliovirus type 2 and rhinovirus type 1A, compared to control plates, when incorporated into agar overlays at a concentration of 50 μg/mL. No cytotoxicity was observed in assays involving this compound at concentrations up to 1 mg/mL.

What is claimed is:

1. A process for preparing a specific inhibitor of proteases which cleave virus-specified polypeptide precursors to form virus-associated proteins, wherein the proteases to be inhibited are specified by a virus selected from the group consisting of picornaviruses, togaviruses, RNA tumor viruses, adenoviruses, comoviruses, and other viruses which encode a viral protease, comprising:
   (a) isolating viral protein, RNA, DNA, mRNA, or DNA complementary to viral RNA;
   (b) analyzing the protein, RNA, DNA, mRNA, or cDNA to provide an amino acid sequence of a polypeptide precursor of virus-specified proteins;
   (c) locating within the amino acid sequence a cleavage recognition site for the virus-specified protease; and
   (d) preparing a specific peptide inhibitor of the virus-specified protease wherein the inhibitor comprises a C-terminal inhibitor moiety selected from the group consisting of halomethyl ketones, covalently linked to a peptide sequence of three to four amino acids or amino acid analogous which substantially corresponds to the amino acid sequence located immediately adjacent to and upstream of the cleavage recognition site of the polypeptide precursor.

2. A process according to claim 1, wherein the peptide sequence of the inhibitor consists of four amino acids or amino acid analogues.

3. A process according to claim 1, wherein the peptide sequence of the inhibitor is exactly homologous to the amino acid sequence located immediately adjacent to and upstream of the cleavage recognition site of the polypeptide precursor.

4. A process according to claim 1, wherein the virus is a picornavirus.

5. A process according to claim 4, wherein the virus is a rhinovirus.

6. A process according to claim 4, wherein the virus is a foot-and-mouth disease virus.

7. A process according to claim 1, wherein the virus is a togavirus.

8. A process according to claim 1, wherein the virus is an RNA tumor virus.

9. A process according to claim 8, wherein the virus is a human T-cell leukemia virus.

* * * * *